United States Patent [19]

Terashima et al.

[11] Patent Number: 5,536,472
[45] Date of Patent: Jul. 16, 1996

[54] CHEMICAL ANALYSIS ELEMENT CARTRIDGE

[75] Inventors: Kaoru Terashima, Saitama-ken; Yoshihiro Seto, Kanagawa-ken; Shigeru Tezuka, Saitama-ken; Seiichi Watanabe, Kanagawa-ken; Yoshihiko Abe, Saitama-ken, all of Japan

[73] Assignee: Fuji Photo Film Co., Ltd., Kanagawa-ken, Japan

[21] Appl. No.: 340,648

[22] Filed: Nov. 16, 1994

[30] Foreign Application Priority Data

Nov. 22, 1993 [JP] Japan .................................. 5-291879
Nov. 22, 1993 [JP] Japan .................................. 5-291880

[51] Int. Cl.⁶ .................................................. G01N 35/00
[52] U.S. Cl. ..................... 422/63; 422/68.1; 422/104; 436/43; 436/46; 221/56; 221/198; 221/226; 221/279
[58] Field of Search .................. 422/63, 64, 65, 422/66, 58, 60, 99, 102, 104, 68.1; 436/43, 44, 46, 47, 48, 49, 170, 805, 807; 221/279, 56, 198, 226

[56] References Cited

U.S. PATENT DOCUMENTS

| | | | |
|---|---|---|---|
| 3,934,753 | 1/1976 | Curtiss . | |
| 3,992,158 | 11/1976 | Przybylowicz et al. . | |
| 4,053,381 | 10/1977 | Hamblen et al. . | |
| 4,151,931 | 5/1979 | Scherer et al. . | |
| 4,187,077 | 2/1980 | Covington et al. | 422/63 |
| 4,279,861 | 7/1981 | Jessop | 422/67 |
| 4,292,272 | 9/1981 | Kitajima et al. . | |
| 4,296,069 | 10/1981 | Smith et al. | 422/64 |
| 4,437,970 | 3/1984 | Kitajima et al. . | |
| 4,477,575 | 10/1984 | Vogel et al. . | |
| 4,568,519 | 2/1986 | Hamilton et al. | 422/64 |
| 5,019,347 | 5/1991 | Hiratsuka et al. . | |
| 5,030,418 | 7/1991 | Miyata | 422/63 |
| 5,075,079 | 12/1991 | Kerr et al. | 422/64 |
| 5,154,889 | 10/1992 | Muraishi | 422/65 |

FOREIGN PATENT DOCUMENTS 0064691 11/1982 European Pat. Off. .
0304838 3/1989 European Pat. Off. .

OTHER PUBLICATIONS

Patent Abstracts of Japan, unexamined applications P section, vol. 9, No. 221, 7 Sep. 1985, p. 23 P386 & JP-A-0-079265 (Fuji Shashin Film K.K.).

*Primary Examiner*—Jill Warden
*Assistant Examiner*—Long V. Le
*Attorney, Agent, or Firm*—McAulay Fisher Nissen Goldberg & Kiel

[57] ABSTRACT

A chemical analysis element cartridge includes a box-like cartridge body in which a plurality of chemical analysis elements are stacked and are taken out through an element take-out port formed at one end of the cartridge body. A pressing member is slidably received in the cartridge body and is brought into contact with the stack of the elements on the side remote from the element take-out port to push the stack of the elements toward the element take-out port. The cartridge body is provided at least in one side wall thereof with a slit which extends in the direction of stack of the elements and the pressing member is provided with an external force receiving portion which is laterally interlocked with an urging member disposed outside the cartridge body through the slit and receives a force for urging the pressing member toward the element take-out port from the urging member. The pressing member is interlocked with an engagement member so that the pressing member and the engagement member are moved toward the element take-out port together with each other when the force from the urging member is acting on the pressing member and the engagement member permits the pressing member to be displaced away from the element take-out port relative to the engagement member when the force from the urging member is released.

8 Claims, 9 Drawing Sheets

CHEMICAL ANALYSIS ELEMENT CARTRIDGE

BACKGROUND OF THE INVENTION

1. Field of the Invention

This invention relates to a chemical analysis element cartridge for storing a plurality of chemical analysis elements, such as those for quantitatively analyzing the content of a specific chemical, biochemical or immunochemical component contained in a sample liquid such as blood or urine and for measuring the concentration (activity) of particular ionic substances in a sample liquid such as blood or urine, and taking out the same one by one.

2. Description of the Prior Art

There has been put into practice various "dry-to-the-touch" chemical analysis elements.

For example, there has been proposed, for instance, in U.S. Pat. Nos. 3,992,158; 4,292,272 and 5,019,347 and European Patent 0 162 302B, and put into practice a "dry-to-the-touch" chemical analysis film with which the content of a specific chemical, biochemical or immunochemical component contained in a sample liquid (hereinafter referred to as an analyte), the activity thereof or the content of a solid component can be quantitatively analyzed by only spotting a droplet of the sample liquid on the film. As such a dry chemical analysis film, there has been known an integrated multi-layered chemical analysis film (sometimes referred to as "multi-layered chemical analysis element") comprising a support sheet of organic polymer and at least one reagent layer which contains a reagent and is formed on the support sheet. A spreading layer is preferably provided over the reagent layer. Further a dry chemical analysis element which is formed of filter paper and has one or more layers has been proposed, for instance, in U.S. Pat. No. 4,477,575, and partly put into practice.

When quantitatively analyzing the chemical, biochemical or immunochemical components or the like contained in a sample liquid using such a dry chemical analysis film, a droplet of the sample liquid is spotted on the film (on the spreading layer when the film is provided with a spreading layer and directly on the reagent layer when the film is not provided with a spreading layer) and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the film is projected onto the film and the optical density of the film is measured. Then the concentration or the activity of the component to be analyzed is determined on the basis of the optical density using a calibration curve which represents the relation between the concentration of the chemical, biochemical or immunochemical component and the optical density.

The integrated multi-layered chemical analysis film is generally in the form of a film chip of a predetermined shape such as square or rectangle. The film chip is sometimes provided with a frame of organic polymer for facilitating automated handling of the chemical analysis film and for flattening the film chip which is apt to be warped (curled or curved) into a roof tile-like shape in a dry state and is used in the form of a chemical analysis slide. In a biochemical analysis apparatus we have proposed previously, the film chip is used as it is without frame (will be referred to as "frameless chemical analysis film", hereinbelow). A plurality of the frameless chemical analysis films are loaded in a cartridge and the cartridge is loaded in a chemical analysis film supplier for a biochemical analysis apparatus. The frameless chemical analysis films are taken out from the cartridge in the supplier one by one.

Use of the frameless chemical analysis film is advantageous over use of the chemical analysis slides in the following point. That is, the chemical analysis slide is larger than the frameless chemical analysis film by the size of the frame and accordingly parts of the biochemical analysis apparatus must be larger, which obstructs reduction in size of the biochemical analysis apparatus and at the same time results in reduction of the overall throughput capacity of the biochemical analysis apparatus. Thus the use of the chemical analysis slides adds to the cost of measurement.

Further there has been proposed, for instance, in U.S. Pat. Nos. 4,053,381 and 4,437,970 and put into practice a "dry-to-the-touch" electrolyte analysis slide for quantitatively analyzing the activity of particular ionic substances contained in a sample liquid such as blood or urine in a potentiometric way. The electrolyte analysis slide is a kind of electrochemical sensors and comprises an ion selective electrode pair.

In this specification, the term "chemical analysis element" should be broadly interpreted to include the chemical analysis slide, the frameless multilayered chemical analysis film, the single-layered or multi-layered chemical analysis element formed of filter paper (with or without frame), and the electrolyte analysis slide described above.

For instance, in Japanese Patent Publication 57(1982)-53271 and U.S. Pat. No. 4,151,931, there is disclosed a chemical analysis element cartridge in which a plurality of chemical analysis elements are stacked and from which the chemical analysis elements are taken out one by one. In the cartridge, a plurality of chemical analysis elements are stacked in a cartridge which is provided with an element take-out port in a side surface of the upper portion of the cartridge, and the uppermost element is pushed out and fed to an analysis apparatus through the element take-out port by a pusher blade which is moved in a horizontal direction. The stack of the elements are supported on a support member which is disposed in the cartridge and is permitted to move only upward by a ratchet mechanism, and the support member is lifted upward by a plunger inserted into the cartridge from below so that the stack of the elements is moved upward by a distance equal to the thickness of one element and the second uppermost element is brought to the element take-out port each time the uppermost element is pushed out.

However this cartridge is disadvantageous in the following points. That is, since the plunger is inserted into the cartridge through an opening formed in the bottom of the cartridge to push upward the support member, thereby urging the stack of the elements toward the take-out port, the stroke of the plunger is long and a long time is required for operation of the plunger. Accordingly when a plurality of elements are taken out from a plurality of cartridges for different analytes, take-out efficiency is low, which makes difficult mass-handling by shortening of the handling time.

Further in order to insert and retract the plunger into and from the cartridge in the vertical direction, a height equal to the sum of the height of the cartridge, the length of the plunger and the stroke of the plunger is required, which adds to the size of the apparatus.

Further in the cartridge described above, the support member is prevented from moving in the reverse direction by the ratchet mechanism. This involves the following problem in the case where the frameless chemical analysis films are stored in the cartridge. That is, the frameless chemical analysis films, which are curled in the dry state as described above, are compressed between the support member and the end wall of the cartridge adjacent to the element take-out port and flattened when urged toward the element take-out port, whereby restoring resilient force is produced and as a result, a larger pressing force acts on the frameless chemical analysis films.

In the case of the frameless chemical analysis films, it is difficult to push out each film from the cartridge by use of a pusher blade such as described above since the films are curled and the state of curl differs from film to film. For example, the films can be taken out by attracting them under a suction force by a suction pad. However since the attracting force under a suction force is limited, it is difficult to surely take out the films when the films are pressed toward the element take-out port under a large pressing force.

Further in the stack of the frameless chemical analysis films, the spreading layer of each film is in a direct contact with the adjacent film and accordingly when the film is pulled out while the films are pressed under a large pressing force, the spreading layer can be rubbed and damaged to such an extent that a desired spreading performance cannot be obtained.

SUMMARY OF THE INVENTION

In view of the foregoing observations and description, the primary object of the present invention is to provide a chemical analysis element cartridge which makes it feasible to take out the chemical analysis elements stored in the cartridge with a high efficiency.

Another object of the present invention is to provide a chemical analysis element cartridge in which the chemical analysis elements stored in the cartridge can be taken out by a small force.

In accordance with one aspect of the present invention, there is provided a dry chemical analysis element cartridge comprising a box-like cartridge body in which a plurality of chemical analysis elements are stacked and are taken out through an element take-out port formed at one end of the cartridge body, and a pressing member which is slidably received in the cartridge body and is adapted to be brought into contact with the stack of the elements on the side remote from the element take-out port to push the stack of the elements toward the element take-out port, wherein the cartridge body is provided at least in one side wall thereof with a slit which extends in the direction of stack of the elements and the pressing member is provided with an external force receiving portion which is laterally interlocked with an urging means disposed outside the cartridge body through the slit and receives a force for urging the pressing member toward the element take-out port from the urging means.

It is preferred that the external force receiving portion be in the form of a rod an end of which extends in the transverse direction of the cartridge body and projects outside the cartridge body through said slit. Further the pressing member may be provided with a mechanism which permits the pressing member to move toward the element take-out port but does not permit the pressing member to move away from the element take-out port.

In the cartridge, the external force receiving portion of the pressing member is projected outside the cartridge body through the slit and interlocked with the urging means outside the cartridge body or the urging means is inserted into the cartridge body through the slit and is interlocked with the external force receiving portion inside the cartridge body. That is, the stack of the chemical analysis elements are urged toward the element take-out port by the urging means which is laterally interlocked with the pressing member or the external force receiving portion of the pressing member. Accordingly, insertion of a plunger having a length equal to the distance by which the stack of the elements is to be fed becomes unnecessary and feed of the chemical analysis elements can be effected with a high efficiency, whereby the chemical analysis elements can be taken out from a plurality of cartridges in a short time. Further the urging means can be simple in structure and small in height, whereby the overall size of the biochemical analysis apparatus can be reduced.

When the pressing member is provided with a mechanism which permits the pressing member to move toward the element take-out port but does not permit the pressing member to move away from the element take-out port, the stack of the elements can be held there even if the urging force from the urging means is released. Accordingly, it is not necessary to normally urge the pressing member by the urging means and the urging means can be simple in structure.

In accordance with another aspect of the present invention, there is provided a dry chemical analysis element cartridge comprising a box-like cartridge body in which a plurality of chemical analysis elements are stacked and are taken out through an element take-out port formed at one end of the cartridge body, a pressing member which is slidably received in the cartridge body and is adapted to be brought into contact with the stack of the elements on the side remote from the element take-out port to push the stack of the elements toward the element take-out port under a force applied thereto from an urging means disposed outside the cartridge body, and an engagement member which is provided in the cartridge body to be movable toward the element take-out port and not to be movable away from the element take-out port, wherein the pressing member and the engagement member are interlocked with each other so that the pressing member and the engagement member are moved toward the element take-out port together with each other when the force from the urging means is acting on the pressing member and the engagement member permits the pressing member to be displaced away from the element take-out port relative to the engagement member when the force from the urging means is released so that the pressing force applied to the stack of the elements from the pressing member is reduced.

For example, the pressing member and the engagement member are separately formed and are interlocked with each other to be slidable relative to each other and the pressing member is slid away from the element take-out port relative to the engagement member when the force from the urging means is released. Otherwise the engagement member may be formed of a spring member and fixedly connected to the pressing member and the pressing member may be displaced away from the element take-out port by deformation of the engagement member when the force from the urging means is released.

In the cartridge, since the pressing member is moved toward the element take-out port together with the engagement member when the external force from the urging means is acting on the pressing member and the pressing member is moved away from the element take-out port while the engagement member is held there when the external force from the urging means is released, the pressing force acting on the stack of the elements is reduced or nullified when the external force applied to the pressing member is released, whereby the chemical analysis elements stored in the cartridge can be taken out by a small force.

DESCRIPTION OF THE PREFERRED EMBODIMENTS

Figure 1:
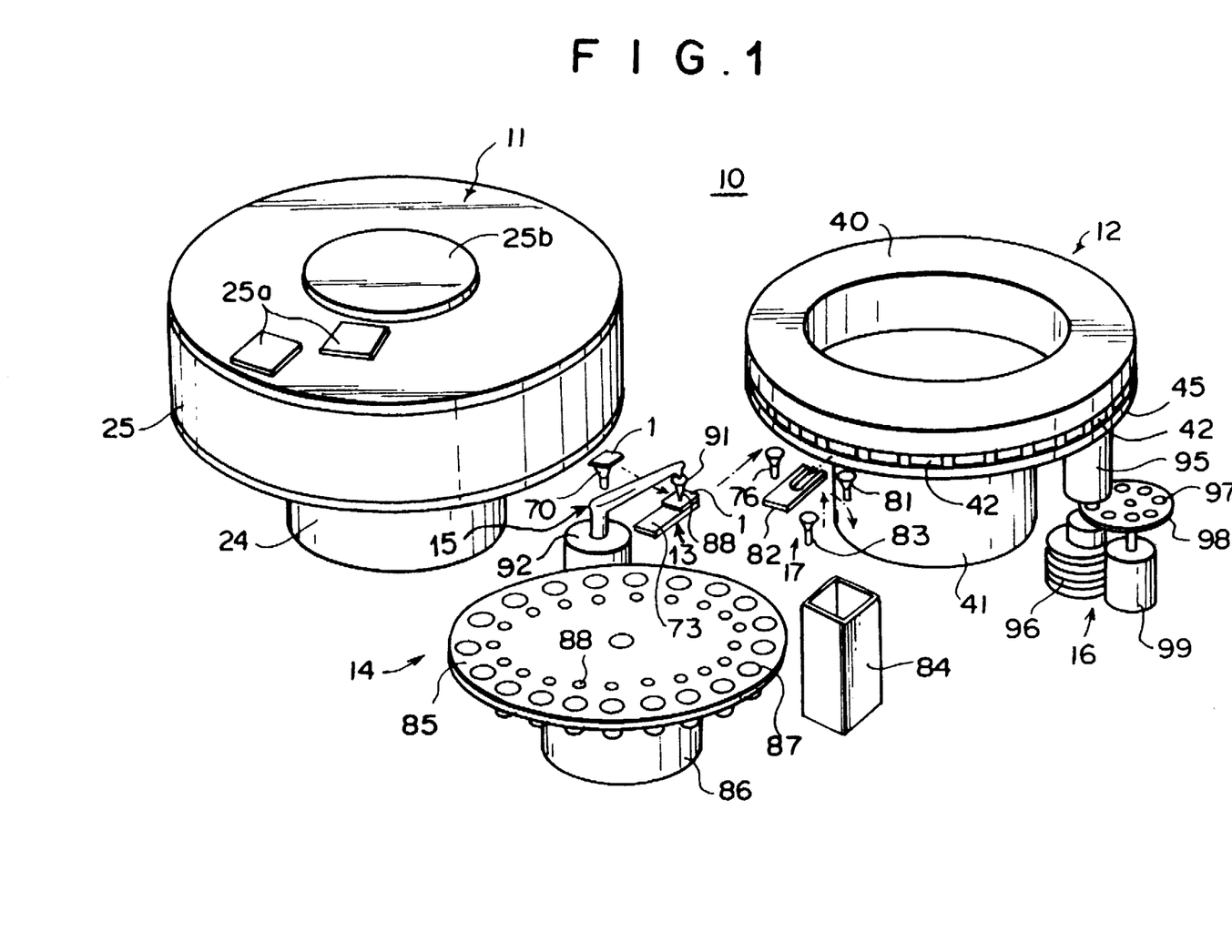
FIG. 1 is a schematic perspective view of a biochemical analysis apparatus provided with a cartridge in accordance with an embodiment of the present invention.

In FIG. 1, a biochemical analysis apparatus 10 provided with a cartridge in accordance with an embodiment of the present invention comprises a film supplier 11 in which a plurality of virgin dry frameless chemical analysis films 1 (which are rectangular or square in shape) are stored, an incubator 12 which is disposed beside the film supplier 11 and incubates the frameless chemical analysis films 1 spotted with sample liquids for a predetermined time at a constant temperature, a film transfer means 13 which transfers the frameless chemical analysis films 1 from the film supplier 11 to the incubator 12, a sample liquid supplier 14 in which a plurality of sample liquids such as whole blood, serum, urine or the like are stored, a spotting mechanism 15 which spots one of the sample liquids in the sample liquid supplier 14 on the frameless chemical analysis film 1 on the way to the incubator 12, and a light measuring system 16 disposed below the incubator 12.

Figure 2A:
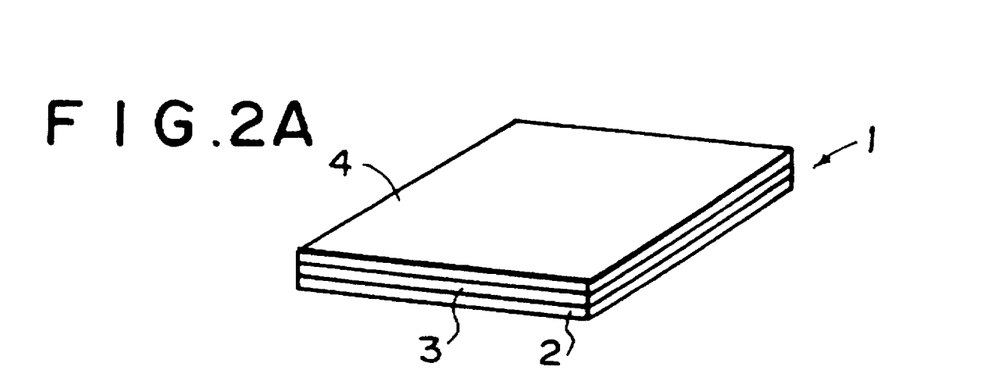
FIGS. 2A to 2C are perspective views showing the frameless chemical analysis film in different states.

As shown in FIG. 2A, the frameless chemical analysis film 1 comprises a light-transmissive support sheet or support sheet 2 formed of plastic film such as polyethylene terephthalate, polystyrene or the like, a reagent layer 3 and a spreading layer 4. That is, the frameless chemical analysis film 1 is formed by coating or bonding the reagent layer 3 on the support sheet 2 and laminating the spreading layer 4 on the reagent layer 3. It should be noted that the film is not provided with any frame.

The reagent layer 3 comprises at least one layer composed of a porous layer or a hydrophilic polymer binder such as gelatin containing therein a detecting reagent component which selectively reacts with an analyte and a reagent component (chemical analysis reagent or immunoassay reagent) which is necessary for coloring reaction.

The spreading layer 4 is formed of a material resistant to rubbing such as woven or knitted fabric (or cloth) of synthetic fiber such as polyester or of blend of natural fiber and synthetic fiber, or paper and functions as a protective layer. Further the spreading layer 4 causes sample liquid applied thereto to uniformly spread over the reagent layer 3.

Figure 2B:
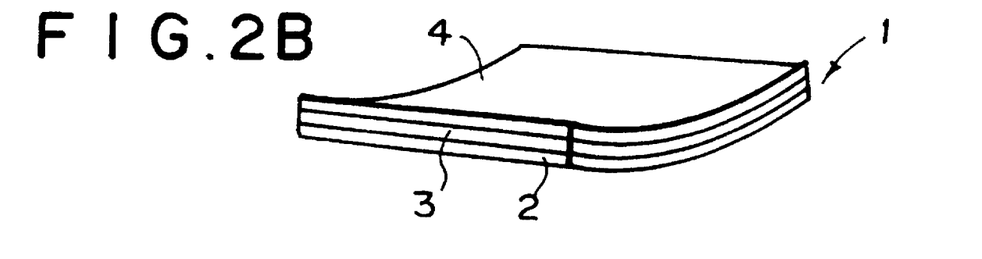
Figure 2C:
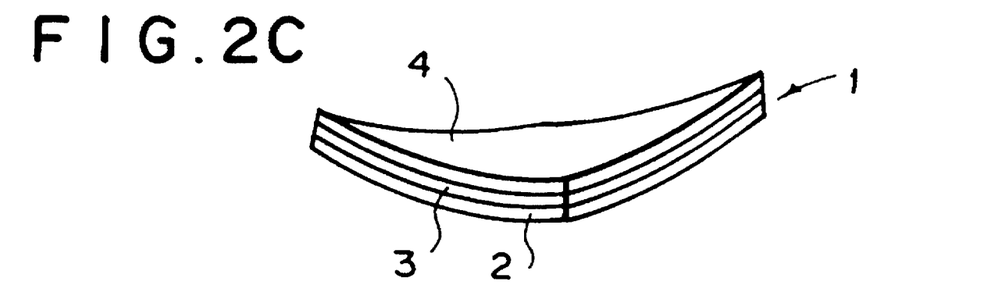

Under the normal humidity conditions the frameless chemical analysis film 1 is substantially flat as shown in FIG. 2A. The film 1 is stored in a dry environment (e.g., in an environment where the humidity is not higher than 20%) in order to suppress chemical reaction or immunoreaction, and in a dry state, the film is warped (curled or curved) toward the spreading layer 4 as shown in FIG. 2B or 2C. In the state shown in FIG. 2B, the film chip 1 is curled in one direction and in the state shown in FIG. 2C, the film chip 1 is curled in a plurality of directions.

The chemical analysis films 1 are stacked in cartridges 20 shown in FIGS. 3 to 6 (6A and 6B) for the respective items of measurement (analytes to be analyzed) with the supports sheets 2 facing downward.

As shown in FIGS. 3 to 6 (6A and 6B), the cartridge 20 comprises a box-like cartridge body 21. The cartridge body 21 is rectangular in cross-section and is divided into left and right halves along a vertical plane at the center thereof. The cartridge body 21 is provided with a film take-out port 22 in one side near the bottom thereof. The film take-out port 22 comprises a first opening 22a which opens in one side of the cartridge body 21 and permits a film 1 to pass therethrough and a second opening 22b which opens in the bottom of the cartridge body 21 and gives access to the lowermost film of the stack of the films 1 to a suction pad 70 which attracts the lowermost film 1 and holds it under a suction force as will be described in detail later.

Figure 3:
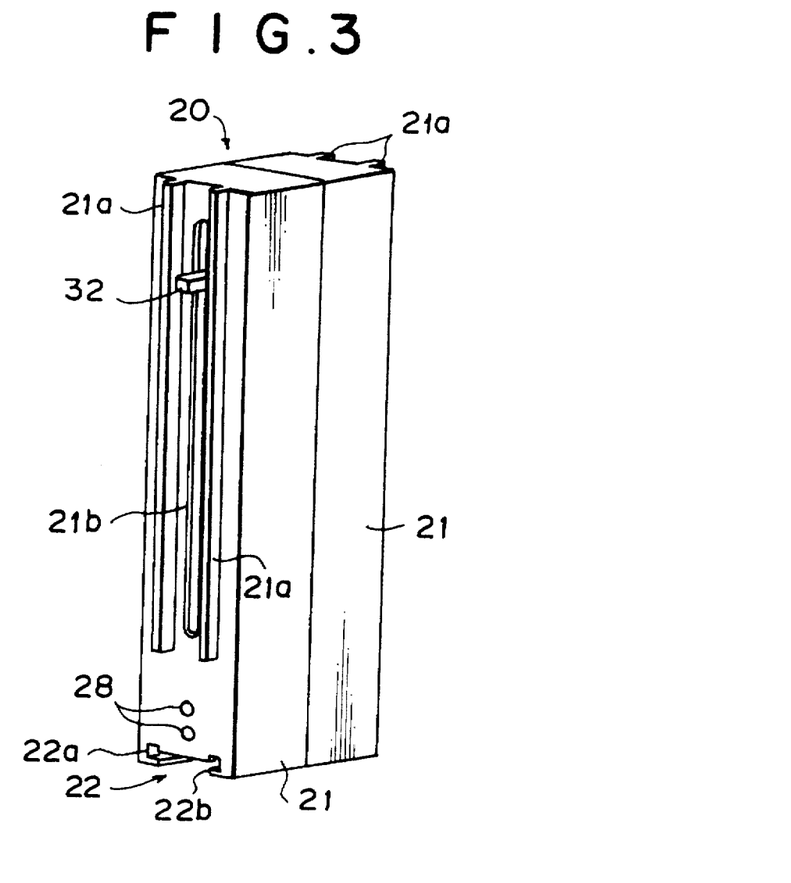
FIG. 3 is a perspective view of the cartridge.
Figure 4:
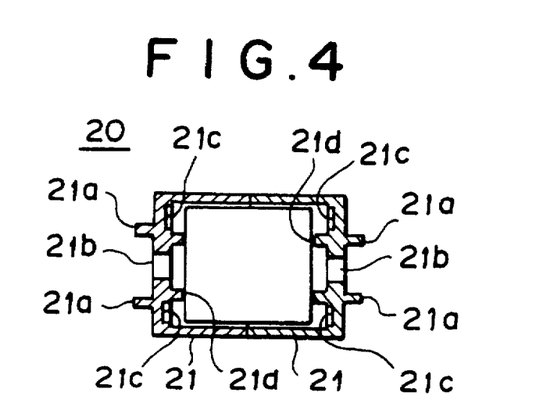
FIG. 4 is a cross-sectional view of the cartridge with the pressing member removed.
Figure 5:
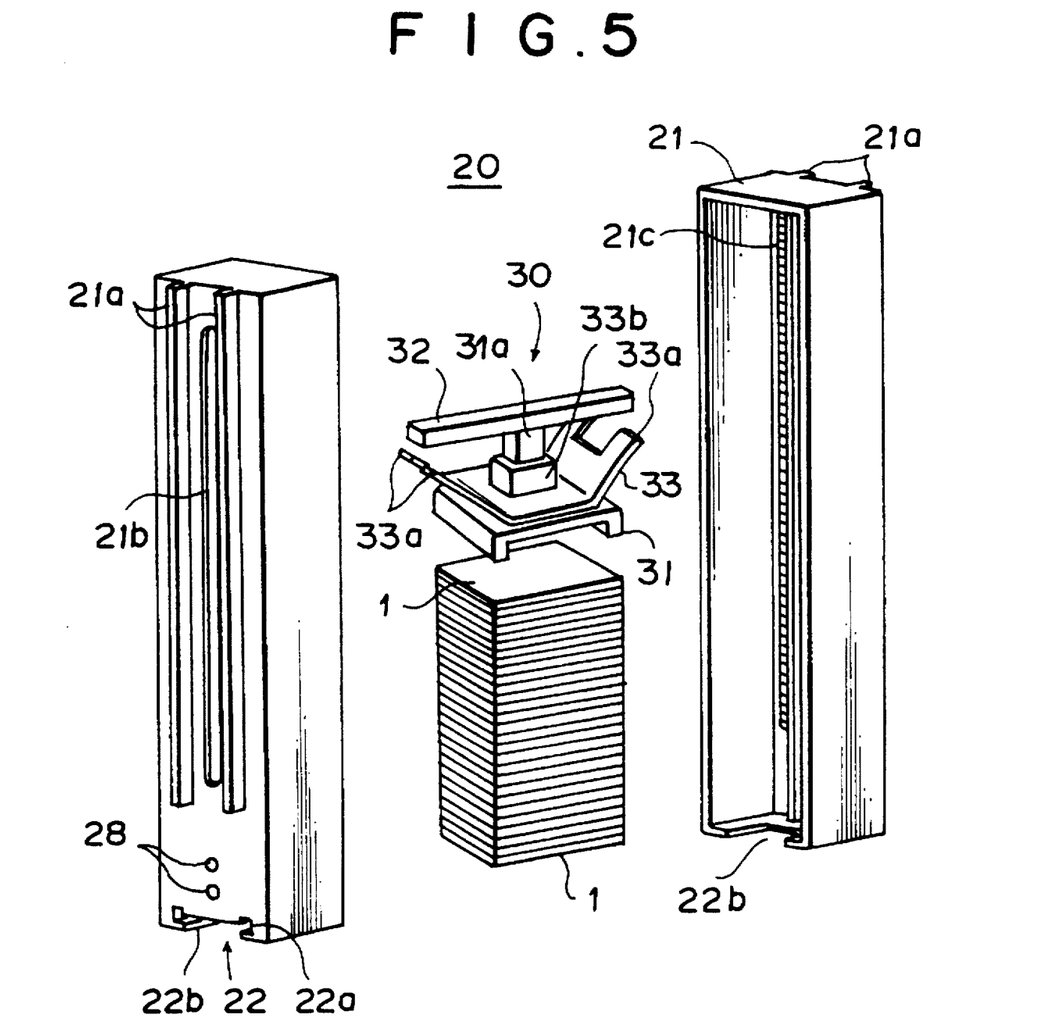
FIG. 5 is an exploded perspective view of the cartridge.

A pair of outer ribs 21a are formed on each of the left and right side walls of the cartridge body 21 to extend in the longitudinal direction of the cartridge body 21. The space between the outer ribs 21a on the left side wall differs from that on the right side wall to prevent insertion of the cartridge 20 into the film supplier 11 in a wrong position. The outer ribs 21a project in the transverse direction of the cartridge body 21 beyond the ends of an external force receiving portion 32 of a film feed mechanism 30 (to be described later) which project from the cartridge body 21 in the transverse direction thereof between the outer ribs 21a and protect the ends of the external force receiving portion 32. Further the outer ribs 21a reinforce the cartridge body 21.

In each of the left and right side walls, a longitudinal slit 21b is formed to extend in the longitudinal direction of the cartridge body 21 between the outer ribs 21a, and a pair of inner ribs 21d are formed on the inner surface of each of the left and right side walls to extend in the longitudinal direction of the cartridge body 21 on opposite sides of the longitudinal slit 21b. Ratchet teeth 21c are formed on the inner surface of each of the left and right side walls to extend along the inner ribs 21d on opposite sides of the inner ribs 21d.

The thickness of the chemical analysis films 1 can differ depending on the analytes to be analyzed and the size of the first opening 22a is set depending on the thickness of the films 1 to be loaded in the cartridge 20 so that the films 1 can be taken out surely one by one through the first opening 22a. In order to check the compatibility of each cartridge body 21 with the films 1 to be loaded therein, distinguishing holes 28 are selectively formed in the left and right side walls. That is, a pair of holes 28a are formed in the left side wall arranged in a vertical direction and no or one or two holes are formed in the right side wall. When one hole is formed in the right side wall, the single hole is formed to be aligned with the upper or lower hole in the left side wall. When two holes are formed in the right side wall, the two holes are formed to be aligned respectively with the upper and lower holes in the left side wall. Detecting light is projected into the holes 28 in the left side wall toward the right side wall and light passing through the holes 28 is received on the right side of the cartridge body 21 by upper and lower photodetectors (not shown). Thus by combinations of the holes 28 formed in the left and right side walls, four thicknesses of the films 1 to be loaded in the cartridge body 21 can be represented, i.e., one for the case where two holes are formed in the right side wall and the detecting light is received by both the upper and lower photodetectors, another for the case where one hole is formed in the right side wall in alignment with the upper hole in the left side wall and the detecting light is received by only the upper photodetector, another for the case where one hole is formed in the right side wall in alignment with the lower hole in the left side wall and the detecting light is received by only the lower photodetector and the other for the case where no hole is formed in the right side wall and the detecting light is received by none of the upper and lower photodetectors.

A feed mechanism 30 for feeding the stack of the films 1 toward the film take-out port 22 is provided in the cartridge body 21. Since the films 1 are taken out through the film take-out port 22 disposed on the lower end of the cartridge body 21 in this embodiment, the force required to take out the film 1 increases as the urging force is larger, which can result in difficulties in taking out the film 1. In order to overcome this problem, the feed mechanism 30 is provided with a pressing force reducing structure for reducing the film pressing force after the stack of the films 1 is pushed toward the film take-out port 22 in response to one film being taken out from the cartridge. In the structure, a restoring resilient force which is produced when the films 1, which are warped or curled into a roof tile-like shape as shown in FIGS. 2B and 2C, are pressed flat is used to reduce the film pressing force as will become apparent later.

That is, the feed mechanism 30 comprises a pressing member 31, said external force receiving portion 32 and an engagement member 33. The pressing member 31 is brought into contact with the uppermost one of the films 1 in the stack and is shaped to contact with the uppermost film at edge portions of the film 1, or at corner portions of the same or over entire area of the same. A rod 31a vertically projects upward from the center of the pressing member 31 and the external force receiving portion 32 is formed integrally with the rod 31a to horizontally extend like a bar from the upper end of the rod 31a in T-shape. Though the engagement member 33 is basically moved integrally with the pressing member 31, the engagement member 33 is incorporated in the feed mechanism 30 to be slidable relative to the pressing member 31 by a limited distance along the rod 31a. Opposite end portions of the external force receiving portion 32 projects outside the cartridge body 21 through the longitudinal slits 21b short of the top of the outer ribs 21a. An urging means 50 urges downward the end portions of the external force receiving portion 32 as will be described later.

The engagement member 33 comprises a boss portion 33b which is formed at the center of a plate-like body portion and is slidably fitted on the rod 31a and a pair of resilient claw portions 33a which extend outwardly upward from opposite ends of the plate-like body portion and engage with the ratchet teeth 21c on the inner side of the cartridge body 21 from below. The ratchet teeth 21c are shaped to engage with the claw portion 33a so as to permit the claw portion 33a to move downward relative to the teeth 21c but not to permit the claw portion 33a to move upward relative to the teeth 21c.

Figure 6A:
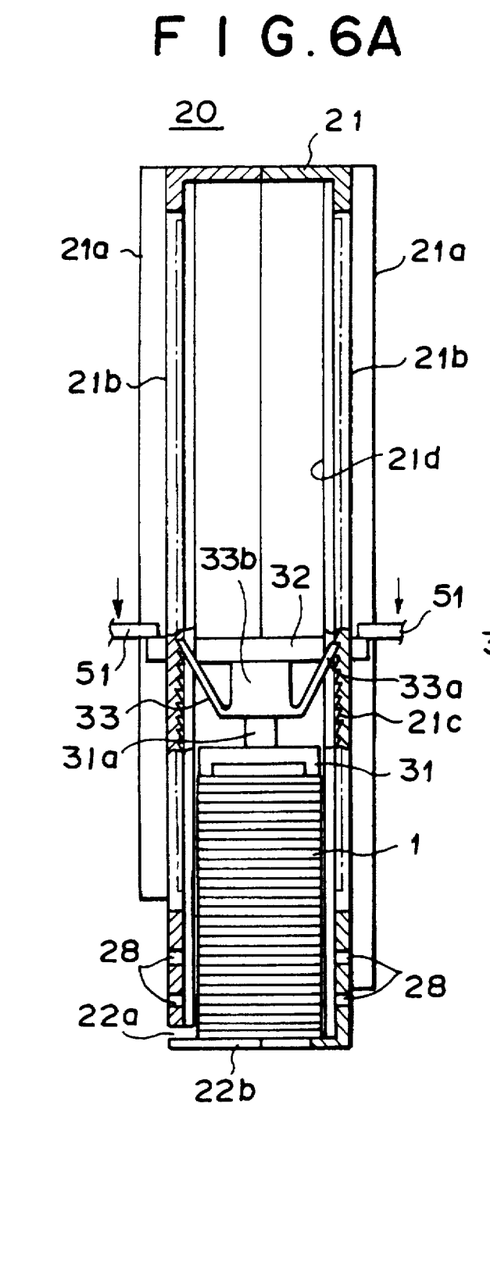
FIGS. 6A and 6B are cross-sectional views for illustrating the operation of the engagement member and the pressing member.

Operation of the feed mechanism 30 will be described with reference to FIGS. 6A and 6B, hereinbelow. FIG. 6A shows a state where an actuator member 51 (to be described later) acts on the end portions of the external force receiving portion 32 to push downward the pressing member 31, thereby pushing the stack of the films 1 toward the film take-out port 22. As can be understood from FIG. 6A, when the actuator member 51 pushes downward the external force receiving portion 32, the pressing member 31 moves downward to push the stack of the films 1 toward the film take-out port 22 and presses the stack against the bottom wall of the cartridge body 21, whereby the films 1 are flattened and the stack of the films 1 is compressed. When the pressing member 31 moves downward, the engagement member 33 is left there until the upper end of the boss portion 33b is brought into abutment against the external force receiving portion 32 due to resistance by engagement of the claw portions 33a and the ratchet teeth 21c and thereafter is moved downward together with the pressing member 31 to be brought into engagement with the ratchet teeth 21c at lower portion thereof. In this state, the engagement member 33 is in contact with the external force receiving portion 32 and away from the pressing member 31 as shown in FIG. 6A, and the film pressing force is enlarged by restoring resilient force of the films 1 produced by flattening the curled films 1.

Figure 6B:
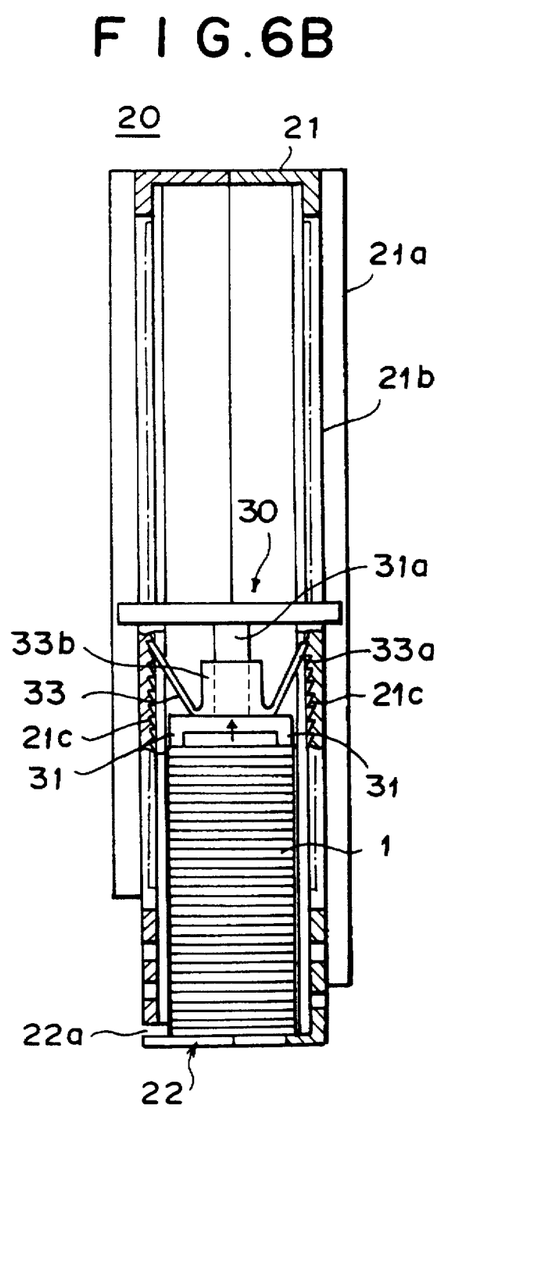

When the external force receiving portion 32 is released from the actuator member 51, the restoring resilient force of the films 1 pushes upward the pressing member 31 and the pressing member 31 is moved upward together with the external force receiving portion 32 until the pressing member 31 is brought into abutment against the bottom of the boss portion 33b of the engagement member 33 which is held stationary by the engagement of the ratchet teeth 21c and the claw portions 33a as shown in FIG. 6B, whereby the pressing force acting on the films 1 is reduced and the film 1 can be easily taken out through the film take-out port 22.

A plurality of the cartridges 20 are respectively loaded in a plurality of cartridge holding portions (not shown) formed in a support member (not shown) in the film supplier 11. The support member is rotated by a supplier motor (not shown) to bring a desired cartridge 20 to a film takeout position where the film transfer means 13 takes out the film 1 in the cartridge 20. After the film 1 is taken out from the cartridge 20, the cartridge 20 is moved to a feed position where an urging means 50 (FIG. 7) causes the feed mechanism 30 to feed downward the stack of the films 1 as will be described later.

The film supplier 11 is provided with a cover 25 which tightly encloses the inner space of the film supplier 11. The cover 25 is provided with a pair of openings 25a provided with lids and the cartridges 20 are taken out and inserted into the cartridge holding portions through the openings 25a. An dehumidifying agent holding portion (not shown) is formed in the support member at the center thereof and dehumidifying agent (desiccant) is loaded in the dehumidifying agent holding portion through an opening 25b formed in the cover 25. The opening 25b is provided with a lid. Thus the inner space of the film supplier 11 is kept within a predetermined humidity range set according to the properties of the films 1.

A shutter (not shown) is provided in the lower surface of the film supplier 11 in the film takeout position. The shutter is opened when the film chip 1 is taken out from the cartridge 20 and a suction pad 70 of the film transfer means 13 takes out the lowermost film 1 in the cartridge 20 through the shutter.

Figure 7:
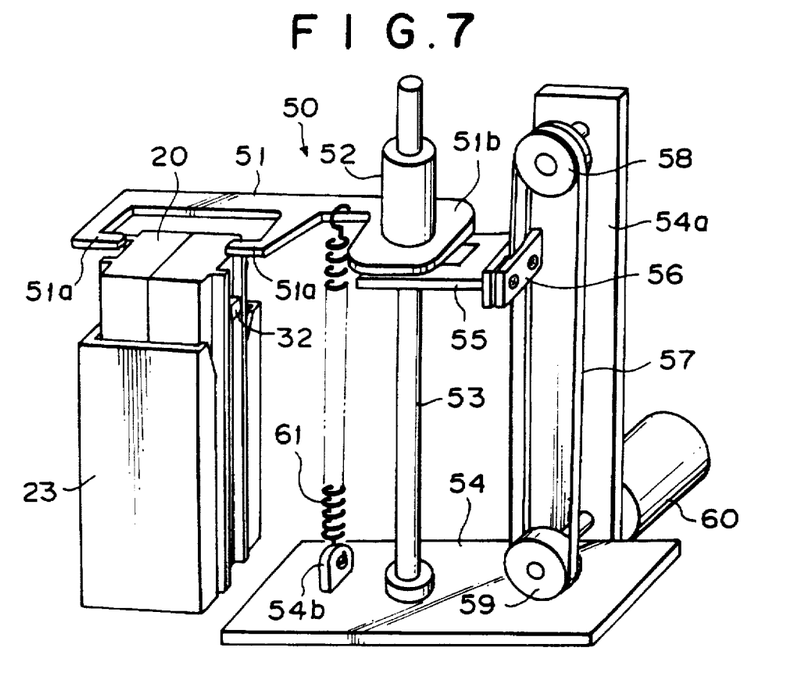
FIG. 7 is a schematic perspective view of the urging means.

An example of the urging means 50 for driving the external force receiving portion 32 of the cartridge 20 will be described with reference to FIGS. 7 and 8, hereinbelow. In FIG. 7, reference numeral 23 denotes a cartridge holding portion formed in the support member in the film supplier 11.

The urging means 50 has said actuator member 51 having a pair of engaging end portions 51a which are adapted to be engaged with the external force receiving portion 32 of the cartridge 20. The actuator member 51 is provided with a sliding tube 52 at a base end portion 51b thereof. The sliding tube 52 is slidably fitted on a guide rod 53 stood on a base 54, whereby the actuator member 51 is supported to be movable up and down along the guide rod 53. The base end portion 51b of the actuator member 51 is supported on a support arm 55 which is fixed to a belt 57 by way of a fixing means 56 at one end. The belt 57 is passed around upper and lower pulleys 58 and 59. The lower pulley 59 is driven by a driving motor 60 to move up and down the support arm 55. The actuator member 51 is normally urged downward by a spring 61 provided between a projection 54b of the base 54 and the actuator member 51. The actuator member 51 is held by the support arm 55 against the urging force of the spring 61.

Figure 8:
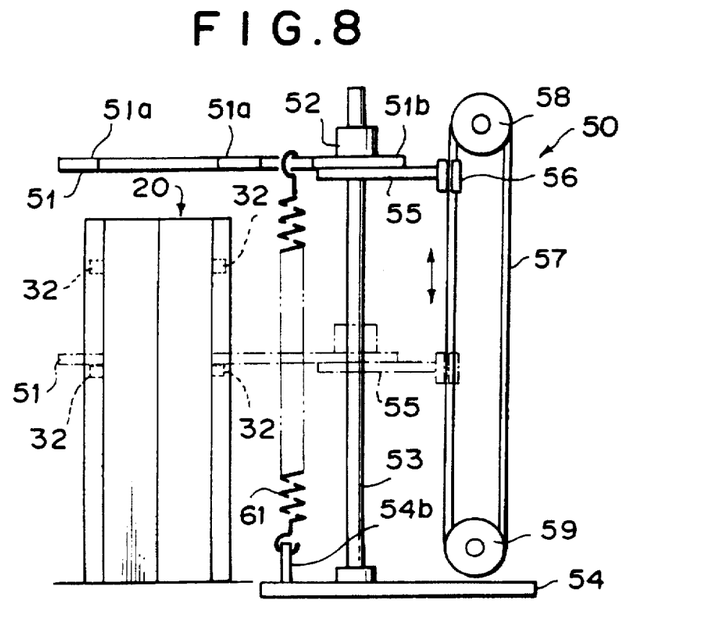
FIG. 8 is a schematic front view of the urging means.

When the support arm 55 is moved downward by the driving motor 60 as shown by the chained line in FIG. 8, the actuator member 51 is moved downward along the guide rod 53 under the force of the spring 61 and the engaging end portions 51a of the actuator member 51 are brought into engagement with the end portions of the external force receiving portion 32, whereby the pressing member 31 presses downward the stack of the films 1 under the force of the spring 61 and feeds it toward the film take-out port 22 as shown in FIG. 6A. After a predetermined pressing, the actuator member 51 is lifted to the position shown by the solid line in FIG. 8 by the driving motor 60 and the external force receiving portion 32 is released from the urging force of the actuator member 51, whereby the pressing force acting on the films 1 is reduced as shown in FIG. 6B. Thereafter another cartridge 20 is brought to the urging means 50 and the similar operation is repeated for the cartridge 20.

The cartridge 20 whose stack of the films 1 has been fed in the manner described above stands by for next take-out of the film 1 and when a film 1 is to be taken out therefrom, the cartridge 20 is moved to the film take-out position. In the film take-out position, the suction pad 70 takes out the film 1 through the film take-out port 22 in the following manner.

Figure 9A:
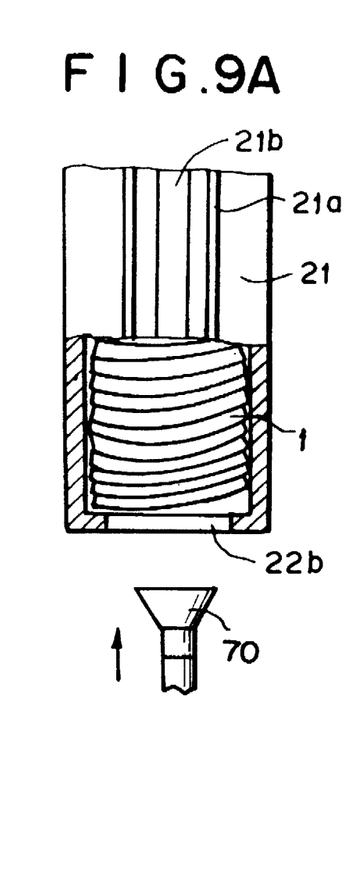
FIGS. 9A to 9D are schematic views for illustrating the procedure of taking out the film from the cartridge.
Figure 9B:
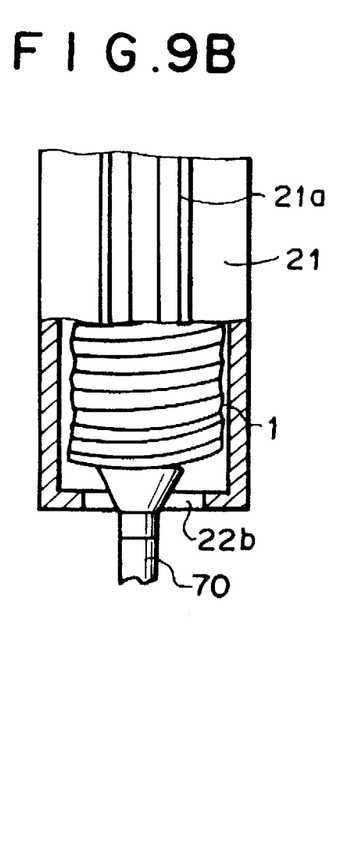

As shown in FIG. 9A, the films 1 are stacked in the cartridge 20 with each of the film chips 1 curled toward the spreading layer 4 to be convex downward and the stack is in the state where the pressing force acting on the films 1 is reduced as shown in FIG. 6B. The suction pad 70 for taking out the film 1 is moved upward and inserted through the second opening 22b of the cartridge body 21 to be brought into abutment against the lowermost film 1 and further moved upward into closer contact with the lowermost film 1 as shown in FIG. 9B. In this position, the suction pad 70 holds the lowermost film 1 under a suction force supplied from a vacuum pump not shown.

Figure 9C:
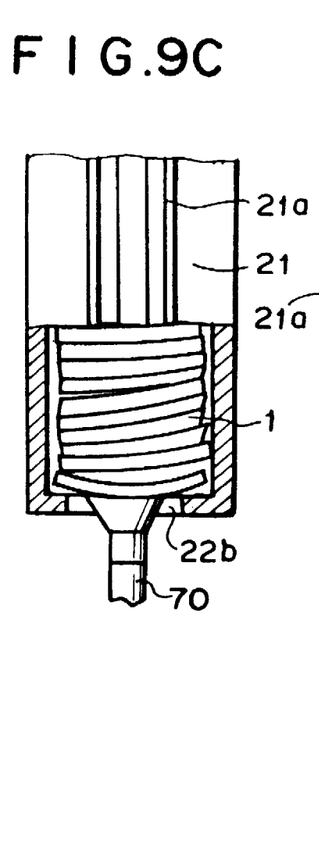

Thereafter the suction pad 70 is moved downward holding the film 1 until the parts of the film 1 on opposite sides of the suction pad 70 is brought into abutment against the edges of the second opening 22b and the film 1 is reshaped into the predetermined warped-shape convex downward as shown in FIG. 9C.

Figure 9D:
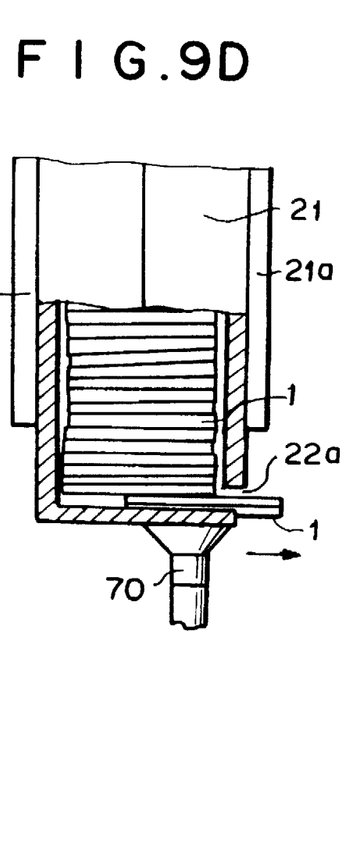

After the reshaping, the suction pad 70 is slid toward the first opening 22a holding the reshaped film 1 to take out the same through the first opening 22a as shown in FIG. 9D. After the film 1 is thus taken out, the cartridge 20 is moved to the feed position and the stack of the films 1 is fed toward the film take-out port 22 by the urging means 50.

The incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The chemical analysis films 1 are incubated in the cells 42.

The body portion 40 comprises a lower disk 45 of metal having a flat upper surface and an upper disk (not shown) of metal provided on the lower disk 45. The peripheral edge portion of the upper disk is bulged upward to form an annular channel open downward. The lower edge of the outer peripheral edge of the upper disk is spaced from the upper surface of the lower disk 45 to form a space which opens in the side surface of the incubator 12 and gives access to the cells 42. A heater (not shown) is disposed in the body portion 40 and the chemical analysis films 1 in the cells 42 are heated to a predetermined temperature (e.g., 37° C.) and held at the temperature.

Though not shown, a plurality of light measuring windows for photometry are formed in the lower disk 45 to be opposed to the respective cells 42, and a film pressing member for fixing the chemical analysis film 1 in a predetermined position in the cell 42 is provided in each of the cells 42. A measuring system 16 has a light measuring head 95 which is disposed below the body portion 40 in a light measuring position.

The film transfer means 13 for transferring the film 1 from the film supplier 11 to the incubator 12 comprises said suction pad 70 for taking out the film 1 from the cartridge 20, a horseshoe-like transfer member 73 which receives the film 1 held on the suction pad 70 from below the film 1 with the spreading layer 4 facing upward and inserts the film 1 into the cell 42 in the incubator 12, and a suction member 76 which moves in and out the cell 42 from below the cell 42 and receives the film 1 held by the transfer member 73 inside the cell 42.

The suction pad 70 is moved up and down and back and forth by a drive mechanism (not shown) to take out the film 1 from the cartridge 20 and transfer the film 1 to the position where the sample liquid is applied on the film 1. The suction member 76 is positioned below the cell 42 in the incubator 12 and is moved up and down by a drive mechanism (not shown) into and away from the cell 42 through the light measuring window.

A film discharge means 17 is disposed in the film discharge position of the incubator 12. The film discharge means 17 comprises a suction pad 81 which attracts the film 1 in the cell 42 which has finished with measurement and lifts it, a horseshoe-like transfer member 82 which receives the film 1 from the suction pad 81 and transfers it outside the incubator 12 and a discarding suction pad 83 which receives the film 1 from the transfer member 82 and discards it into a discarding box 84.

The sample liquid supplier 14 comprises a turn table 85 which is rotated by a drive mechanism 86. The turn table 85 holds a plurality of sample containers 87 filled with sample liquids which are arranged along the circumferential edge of the turn table 85 and is rotated to bring the sample containers 87 to a sample liquid supplying position one by one. A plurality of nozzle tips 88 which are mounted on a spotting nozzle 91 to be described later are held on the turn table 85 inside the sample containers 87.

The spotting means 15 for applying the sample liquid to the film 1 comprises a spotting nozzle 91 which sucks and discharges the sample liquid, and a nozzle tip 88 like a pipette is demountably mounted on the nozzle 91. The nozzle 91 is moved up and down and rotated by a drive mechanism 92. That is, the nozzle 91 sucks the sample liquid from the sample liquid supplier 14, is moved to the film 1 held by the transfer member 73, and then applies the sample liquid to the film 1. The nozzle tip 88 is changed every time the sample liquid is changed.

The film 1 applied with the sample liquid is transferred to the incubator 12 and incubated there. After incubation for a predetermined time, the optical density of the reagent layer 3 is measured by the light measuring system 16 disposed below the incubator 12. The light measuring system 16 comprises said light measuring head 95 for measuring the optical density of the color formed by the coloring reaction between the reagent layer 3 and the analyte in the sample liquid. The light measuring head 95 projects measuring light containing light of a predetermined wavelength onto the reagent layer 3 through the support sheet 2 and detects reflected light with a photodetector. Light from a light source (lamp) 96 enters the light measuring head 95 through an interference filter 97 and is caused to impinge upon the reagent layer 3 by the head 95. A plurality of kinds of filters 97 are mounted on a rotary disk 98 which is driven by an electric motor 99 and one of the filters 97 is selected according to the analyte.

A diffraction grating may be used instead of the interference filter 97 as a spectral means employed in the optical system for projecting the measuring light.

The reflected light from the reagent layer 3 carries thereon optical information (more particularly the amount of light) on the amount of coloring substances formed by the coloring reaction between the reagent layer 3 and the sample liquid. The reflected light is received by the photodetector and the optical information carried by the reflected light is converted to an electric signal by the photodetector. The electric signal is input into a determination section through an amplifier. The determination section determines the optical density of the coloring substances formed by the coloring reaction between the reagent layer 3 and the sample liquid on the basis of the level of the electric signal and determines the concentration or the activity of a predetermined chemical, biochemical or immunochemical component (an analyte) in the sample liquid by colorimetry.

The measurement by the biochemical analysis apparatus 10 is effected in the following manner. That is, a cartridge 20 (in the film supplier 11) storing therein chemical analysis films 1 corresponding to the analyte to be analyzed is moved to the film take-out position. In the cartridge 20, the pressing force acting on the films 1 has been reduced. In the film take-out position, a film 1 is taken out by the suction pad 70 of the transfer means 13. The cartridge 20 is subsequently moved to the feed position and the stack of the films 1 are fed toward the film take-out port 22 by the urging means 50.

The film 1 held by the suction pad 70 is transferred to the transfer member 73 with the reagent layer 3 facing upward and a sample liquid is applied to the reagent layer 3. That is, a nozzle tip 88 is mounted on the spotting nozzle 91 of the spotting means 15 and the spotting nozzle 91 is moved above a desired sample container 87 in the sample liquid supplier 14. Then the nozzle 91 is moved downward to bring the nozzle tip 88 into the sample liquid and the nozzle 91 sucks a predetermined amount of the sample liquid into the nozzle tip 88. Thereafter the nozzle 91 is moved above the center of the film 1 on the transfer member 73 and moved downward toward the film 1, where a predetermined amount of sample liquid is applied to the reagent layer 3 from the nozzle tip 88. The sample liquid spreads over the reagent layer 3 and mixes with the reagent therein.

The film 1 applied with the sample liquid is inserted into one of the cells 42 of the incubator 12 by the transfer member 73.

Coloring reaction (coloring substance forming reaction) is caused when the film 1 with the sample liquid is heated to a predetermined temperature in the enclosed cell 42 in the incubator 12, and the optical density of the coloring substances is measured by the light measuring head 95 after a predetermined time or at predetermined intervals.

Figure 10:
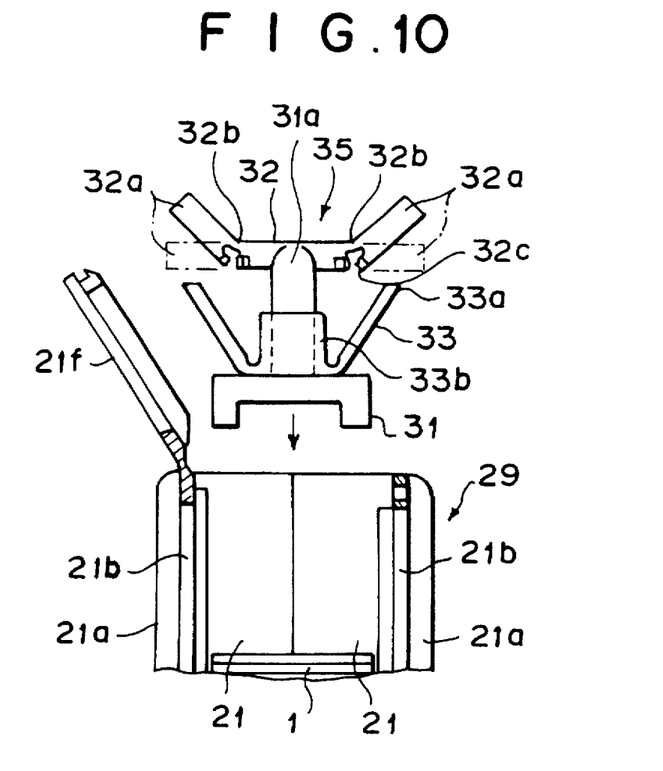
FIG. 10 is a fragmentary front view partly in cross-section showing a modification of the cartridge.

FIG. 10 shows a modification of the cartridge 20. In the cartridge 29 of this modification, the cartridge body 21 is divided into left and right halves as in the preceding embodiment. In this embodiment, the upper end of the cartridge body 21 is open and can be opened closed by a lid member 21f hinged to the left half of the cartridge body 21. The other parts of the cartridge body 21 are substantially the same as those of the cartridge body 21 in the preceding embodiment.

In the feed mechanism 35 of this modification, opposite end portions 32a of the external force receiving portion 32 extending in the horizontal direction are bendable at hinge portions 32b. Each end portion 32a has a resiliency to return to the horizontal position and an engagement portion 32c is provided on the opposite side of the hinge portion 32b to hold the end portion 32a in the horizontal position. The arrangement of the pressing member 31, the engagement member 33 and the like is substantially the same as that in the preceding embodiment.

In this modification, with the lid 21f of the cartridge body 21 opened, the chemical analysis films 1 are stacked in the cartridge body 21 through the opening at the upper end of the cartridge body 21 and then the feed mechanism 35 is inserted into the cartridge body 21 through the opening with the end portions 32a of the external force receiving portion 32 bent upward. When the external force receiving portion 32 reaches the upper end of the longitudinal slits 21b, the end portions 32a of the external force receiving portion 32 returns toward the horizontal position under their own resiliency and project outward through the slits 21b. At the same time the claw portions 33a of the engagement member 33 are brought into engagement with the ratchet teeth 21c. When the end portions 32a of the external force receiving portion 32 are subsequently pushed downward, the engagement portions 32c are engaged and the external force receiving portion 32 becomes straight to extend in the horizontal direction. In this state, the external force receiving portion 32 can be urged by the actuator member 51 of the urging means 50. In this modification, assembly of the cartridge 29 and loading of the films 1 are facilitated.

Figure 11:
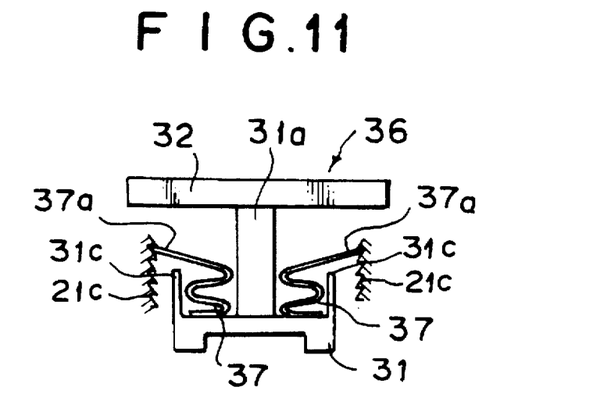
FIG. 11 is a front view of a modification of the feed mechanism.

FIG. 11 shows a modification of the feed mechanism. Though the preceding embodiment is arranged to reduce the pressing force acting on the films 1 by moving the pressing member 31 relative to the engagement member 33, the pressing force is reduced by use of a spring member in this modification.

That is, the feed mechanism 36 of this modification, the pressing member 31 which is brought into contact with the upper surface of the stack of the films 1 has a rod 31a extending upward and an external force receiving portion 32 is formed to horizontally extend from the top of the rod 31a. A pair of engagement members 37 formed of a spring member and having claw portions 37a to be engaged with the ratchet teeth 21c are disposed on opposite sides of the rod 31a. Each engagement member 37 has a corrugate base portion at which the engagement member 37 is fixed to the pressing member 31 and an upper portion which extends outwardly upward and forms the claw portion 37a. An engagement plate 31c extends upward from each side of the pressing member 31 toward the claw portion 37a to prevent reverse movement of the pressing member 31.

In this modification, when the end portions of the external force receiving portion 32 are pushed downward, the pressing member 31 pushes downward the stack of the films 1 while the corrugate portions of the engagement members 37 are stretched and the engaging position between the ratchet teeth 21c and the claw members 37 is shifted downward while the claw portions 37a are deformed to stand toward the vertical. When the urging force on the external force receiving portion 32 is released, the pressing member 31 is moved upward by the restoring force of the films 1 with the claw members 37a kept engaged with the ratchet teeth 21c while the corrugate bases are contracted and the claw portions 37a are deformed to incline from the vertical, whereby the pressing force acting on the films 1 is reduced. The upward movement of the pressing member 31 is limited by abutment of the engagement plates 31c against the claw portions 37.

Figure 12:
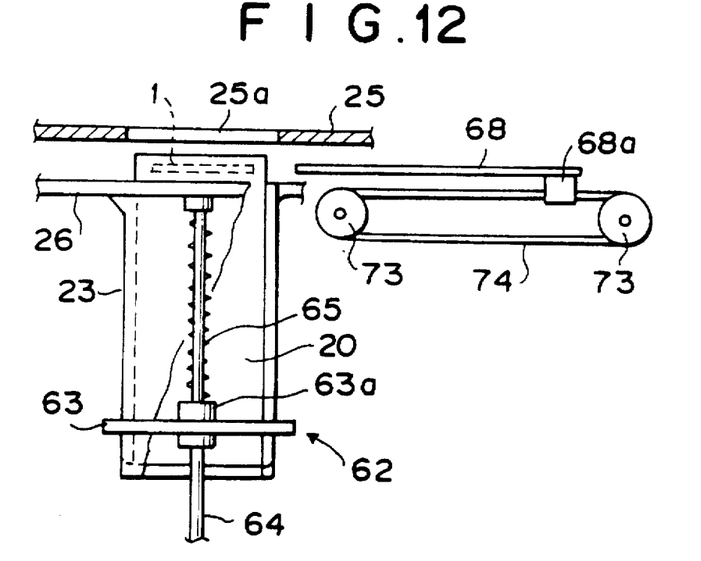
FIG. 12 is a front view showing a cartridge in accordance with another embodiment of the present invention together with a film take-out mechanism.
Figure 13A:
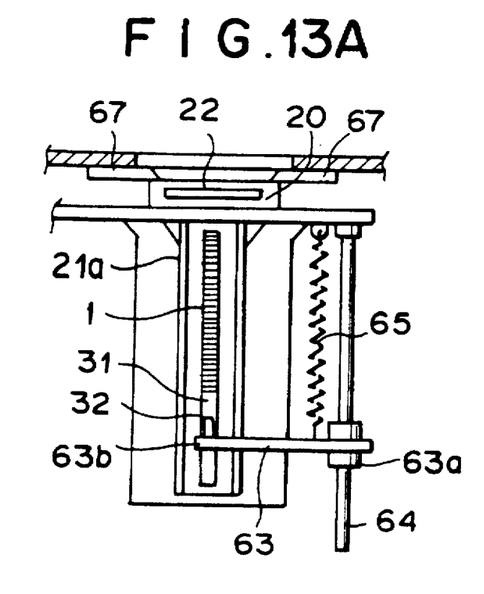
FIGS. 13A and 13B are schematic side views for illustrating the procedure of loading the cartridge in the film supplier.
Figure 13B:
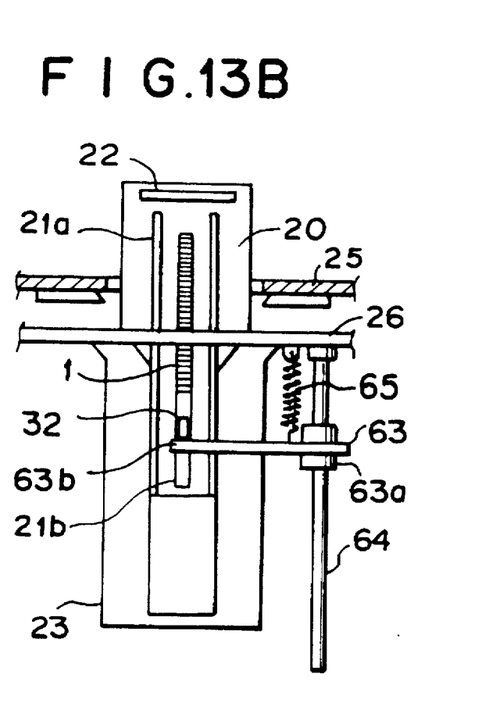

FIGS. 12, 13A and 13B show a cartridge in accordance with another embodiment of the present invention and an urging means to be interlocked with the cartridge. The cartridge 20 of this embodiment is loaded in the film supplier 11 so that the films 1 are taken out from above. Though the cartridge 20 of this embodiment somewhat differs from that of the preceding embodiment, the parts analogous to those of the preceding embodiments are given the same reference numerals.

In the cartridge 20 of this embodiment, a pair of film take-out ports 22 (FIGS. 13A and 13B) are formed in an upper part of the front and rear walls of a rectangular cartridge body 21 in alignment with each other. Outer ribs 21a and the longitudinal slits 21b are formed in the left and right side wall as in the preceding embodiment. A pressing member 31 is disposed on the bottom of the cartridge body 21 and the films 1 are stacked on the pressing member 31. End portions of the external force receiving portion 32 projects outward through the longitudinal slits 21b. The cartridge 20 is inserted into a cartridge holding portion 23 formed in the support member 26 in the film supplier 11 through opening 25a in the cover 25.

In this embodiment, the urging member 62 comprises a support member 63 disposed on the cartridge holding portion 23 to be movable up and down. The support member 63 comprises a boss portion 63a and a pair of engagement portions 63b which extend in parallel to the left and right side wall of the cartridge 20 from opposite end portions of the boss portion 63a and are brought into engagement with the end portions of the external force receiving portion 32. A spring 65 provided between the support member 26 in the film supplier 11 and the support member 63 of the urging means 62 urges upward the support member 63.

A pusher blade 68 (FIG. 12) of a film take-out mechanism is opposed to one of the film take-out ports 22 (inlet side film take-out port 22) respectively formed in the front and rear walls of the cartridge body 21 to be movable into and away from the film take-out port 22. That is, the pusher blade 68 is fixed to a belt 74 by a fastener 68a and the belt 74 is passed around the pulleys 73 and driven by the pulleys 73 to move the pusher blade 68 into and away from the inlet side film take-out port 22.

Though not shown, it is preferred that a guide member for guiding the blade 68 into the inlet side film take-out port 22 be provided inside the film take-out port 22 in order to surely insert the blade 68 into the film take-out port 22, and a cover member for preventing the film 1 from dropping off the cartridge body 21 be provided on the side of the other film take-out port 22.

The cartridge 20 of this embodiment is inserted into the cartridge holding portion 23 in the film supplier 11 through the opening 25a in the cover 25 of the film supplier 11 with the film take-out ports 22 up. When the cartridge 20 is inserted into the film holding portion 23, the external force receiving portion 32 is brought into engagement with the engagement portions 63b of the support member 63 and the cartridge 20 is further moved downward pushing downward the support member 63 overcoming the force of the spring 65.

When the cartridge 20 is completely inserted into the cartridge holding portion 23, a stopper 26 is moved above the cartridge 20 to prevent upward movement of the cartridge 20. In this state, the urging force of the spring 65 normally acts on the stack of the films 1 by way of the pressing member 31 and the stack of the films 1 is urged toward the film take-out ports 22. In this state, the pusher blade 68 is inserted into the cartridge 20 through the inlet side film take-out port 22 and pushes the uppermost film in the stack outside the cartridge 20 through the outlet side film take-out port 22.

In this embodiment, the stack of the films 1 is normally urged by the spring 65 and the mechanism for reducing the pressing force acting on the stack employed in the preceding embodiment is not necessary. Accordingly the pressing member 31 and the external force receiving portion 32 need not be provided with a mechanism for permitting the engagement member 33 to slide relative to the pressing member 31 and the external force receiving portion 32, and the engagement member 33 may be fixed to the pressing member 31 or may be formed integrally with the pressing member 31.

In the embodiments described above, the end portions of the external force receiving portion 32 project outside the cartridge body 21 through the longitudinal slits 21b and the urging means acts on the external force receiving portion 32 through the end portions. However the structure for interlocking the urging means with the external force receiving portion 32 may be variously modified.

For example, instead of so arranging the external force receiving portion that the end portions of the external force receiving portion projects outside the cartridge body 21, the urging means may be arranged so that the end portions of the urging means is inserted into the cartridge body 21 through the longitudinal slits 21b of the cartridge body 21 and is directly engaged with the external force receiving portion inside the cartridge body 21. Further, the longitudinal slit 21b may be formed only in one side wall of the cartridge body 21 so that only one end portion of the external force receiving portion 32 projects outside the cartridge body 21 and the urging means acts on the external force receiving portion 32 through the single end portion or one end portion of the urging means is inserted into the cartridge body 21 through the single longitudinal slit 21b.

Though, in the embodiments described above, the frameless chemical analysis films are loaded in the cartridge as the chemical analysis elements, the chemical analysis slides, the single-layered or multi-layered chemical analysis elements formed of filter paper, the electrolyte analysis slides and the like may be loaded in the cartridge of the present invention without being limited to the frameless chemical analysis films. The cartridge shown in FIGS. 12, 13A and 13B which is not provided with the mechanism for reducing the pressing force acting is especially suitable for loading the slide type chemical analysis elements such as the chemical analysis slides and the electrolyte analysis slides which are flat.

As can be understood from the description above, the stack of the chemical analysis elements are urged toward the element take-out port formed in one end of the cartridge body by the urging means which acts on the pressing member from the a side of the cartridge body through the longitudinal slit. Accordingly, the distance by which the urging means is moved when feeding the stack of the elements is short and the film feeding operation can be effected with a high efficiency, whereby the elements can be taken out in a short time, the mechanisms for taking out the elements can be simple in structure and the biochemical analysis apparatus can be compact in size. Further, in the embodiment where the mechanism for reducing the pressing force acting on the stack is provided, even the frameless chemical analysis films in the curled state can be taken out by a small force by virtue of the mechanism, whereby the films can be stably taken out by a suction pad and fear of the spreading layer being rubbed and damaged during take-out can be eliminated, while the stack of the frameless chemical analysis films can be stably fed toward the element take-out port and surely held there by virtue of the engagement member.

What is claimed is:

1. A dry chemical analysis element cartridge comprising:
   a cartridge body in which a plurality of chemical analysis elements are stacked and are taken out through an element take-out port formed at one end of the cartridge body, and
   a pressing member which is slidably received in the cartridge body and is adapted to be brought into contact with the stack of the elements on a side thereof remote from the element take-out port to push the stack of the elements toward the element take-out port, wherein
   the cartridge body is provided at least in one side wall thereof with a slit which extends in the direction of stack of the chemical analysis elements and the pressing member is provided with an external force receiving portion which extends laterally outwardly through the slit and is operatively interlocked outside of the cartridge body with an urging means disposed outside the cartridge body for applying a force to the pressing member via the external force receiving portion to urge the pressing member toward the element take-out port.

2. A dry chemical analysis element cartridge as defined in claim 1 in which said external force receiving portion is a rod having an end which extends in a transverse direction relative to the cartridge body and projects outside the cartridge body through said slit.

3. A dry chemical analysis element cartridge as defined in claim 1 in which said pressing member is provided with a mechanism which permits the pressing member to move toward the element take-out port but does not permit the pressing member to move away from the element take-out port.

4. A dry chemical analysis element cartridge comprising:
   a cartridge body in which a plurality of chemical analysis elements are stacked and are taken out through an element take-out port formed at one end of the cartridge body,
   a pressing member which is slidably received in the cartridge body and is adapted to be brought into contact with the stack of the elements on a side thereof remote from the element take-out port to push the stack of the elements toward the element take-out port under a force applied thereto from an urging means disposed outside the cartridge body, and
   an engagement member which is provided in the cartridge body to be movable toward the element take-out port and not to be movable away from the element take-out port, wherein
   the pressing member and the engagement member are interlocked so that the pressing member and the engagement member are moved toward the element take-out port together when the force from the urging means is acting on the pressing member and the engagement member permits the pressing member to be displaced away from the element take-out port relative to the engagement member when the force from the urging means is released so that the pressing force applied to the stack of the elements from the pressing member is reduced.

5. A dry chemical analysis element cartridge as defined in claim 4 in which the pressing member and the engagement member are separately formed and are interlocked with each other to be slidable relative to each other, the pressing member being slid away from the element take-out port relative to the engagement member when the force from the urging means is released.

6. A dry chemical analysis element cartridge as defined in claim 4 in which the engagement member is formed of a spring member and is fixedly connected to the pressing member and the pressing member is displaced away from the element take-out port by deformation of the engagement member when the force from the urging means is released.

7. A dry chemical analysis element cartridge as defined in claim 1 in which the external force receiving portion is connected to the pressing member via a rod extending in the direction of stack of the chemical analysis elements.

8. A dry chemical analysis element cartridge as defined in claim 7 in which said rod projects centrally from the pressing member.

* * * * *